United States Patent [19]

Nilsson

[11] Patent Number: 5,246,840

[45] Date of Patent: Sep. 21, 1993

[54] METHOD FOR SYNTHESIS OF OLIGOSACCHARIDES

[75] Inventor: Kurt G. I. Nilsson, Lund, Sweden

[73] Assignee: Procur AB, Lund, Sweden

[21] Appl. No.: 603,699

[22] PCT Filed: Mar. 22, 1989

[86] PCT No.: PCT/SE89/00151

§ 371 Date: Nov. 16, 1990

§ 102(e) Date: Nov. 16, 1990

[87] PCT Pub. No.: WO89/09275

PCT Pub. Date: Oct. 5, 1989

[30] Foreign Application Priority Data

Mar. 24, 1988 [SE] Sweden ................................ 8801080

[51] Int. Cl.$^5$ ...................... C12P 19/04; C12P 19/12; C07H 3/06

[52] U.S. Cl. .................................. 435/101; 435/100; 435/200; 435/74

[58] Field of Search ................... 435/101, 200, 100, 74

[56] References Cited

U.S. PATENT DOCUMENTS 4,918,009 4/1990 Nilsson .............................. 435/200

FOREIGN PATENT DOCUMENTS

87/05936 10/1987 World Int. Prop. O. .

OTHER PUBLICATIONS

Devivar, R. V. et al., "The Formation of an Unusual Product During Studies on the Diazotization of Certain 2-Aminobenzimidazoles," American Chemical Society.
Saluja, S. et al., "Synthesis and Antiviral Activity of Certain 2-Substituted 4,5,6,7-Tetrachlorobenzimidazole Acyclic Nucleosides," American Chemical Society.
Zou, R., "Synthesis and Antiviral Activity of 1-D-Robofuranosyl-2,4,6-Tri-Chlorobenzimidazole," American Chemical Society.
Smith, C. M. et al., "Inhibitors of Hypoxanthine Metabolism in Ehrlich Ascites Tumor Cells in Vitro," *Cancer Treat Rep.*, 60:1567-1584 (1976).
Tamm, I., "Inhibitor of Influenza and Mumps Virus Multiplication by 4,5,6,-(or 5,6,7,-) Tri-chloro-1-D-Ribofuranosyl-benzimidazole," *Science*, 120:847-848 (1954).
Townsend, L. B. "Benzimidazole Nucleosieds, Nucleotides, and Related Derivatives," *Chemical Reviews*, 70:389-438 (1970).
Biosis number 71035393, M. K. A. Markwell et al., "Sendai virus utilizes specific sialyl oligo saccharides as host cell receptor determinants" (Proc. Nat'l Acad. Sci. USA, vol. 77, pp. 5693-5697 (Abstract)).
Paulson, J. C., et al., "Sialyl-and Fucosyltransferases in the Bio-synthesis of Asparaginyl-liked Oligosaccharides in Glycoproteins", J. Biol. Chem. (1978), vol. 253, pp. 5617-5624.
Closs, G. L. et al. "Enzyme-Catalyzed Synthesis of N-Acetyllactosamine with in Situ Regeneration of Uridine 5'-Diphosphate Galactose", *Journal of Organic Chemistry* (1982), vol. 47, pp. 5416-5418.
Rosevear, P. R. et al., "Synthesis and Solution Conformation of the Type 2 Black Gropu Oligosaccharide αLFuc (1→2) βDGal (1→4) βDG1cNac", *Biochemistry* (1982), vol. 21, pp. 1421-1431.
Sabesan, S., et al., "Combined Chemical and Enzymatic Synthesis of Sialyloligosaccharides and Characterization by 500-MHz $^1$H and $^{13}$C NMR Spectroscopy", *J. Am Chem. Soc.* (1986), vol. 108, pp. 2068-2080.
Thiem J., et al., "Synthesis of the Trisaccharide Neu-5-Ac-α(2→6) Gal-β(1→4) GlcNAc by the Use of Immobilized Enzymes", *Angew. Chem. Int. Ed. Engl.* (1986), vol. 25, pp. 1096-1097.
Paulson, J. C., et al., "Use of Glycosyltransferases and Glycosidases in Structural Analysis of Oligosaccharides", Glycoconjugate Research (1979) vol. 1, pp. 247-250.

*Primary Examiner*—Ronald W. Griffin
*Assistant Examiner*—Pamela S. Webber
*Attorney, Agent, or Firm*—Beveridge, DeGrandi, Weilacher & Young

[57] ABSTRACT

A method for synthesis of oligosaccharide compounds which either consist of or are fragments or analogs of the carbohydrate part in glycoconjugates is described. The synthesis from donor and acceptor substrates is carried out in that at least one glycosidase and at least one glycosyltransferase are used as catalysts and the oligosaccharide compound is isolated from the reaction mixture.

11 Claims, No Drawings

METHOD FOR SYNTHESIS OF OLIGOSACCHARIDES

DESCRIPTION

The present invention relates to a method for enzymatic synthesis of an oligosaccharide compound, which either consists of or is a fragment or an analog of the carbohydrate part in a glycoconjugate. Furthermore, the invention relates to the use of the product prepared by this method.

It has been found that the oligosaccharide part of various glycoconjugates (especially glycolipids and glycoproteins) have a number of important functions in vivo (Biology of Carbohydrates, Vol. 2., Ginsburg et al., Wiley, New York (1984); The Glycoconjugates, Vol. 1-V, Academic Press, New York; S. Hakomori, Ann. Rev. Biochem. Vol. 50, pp. 733-64); Feizi, Nature, pp. 314 (1985); S. Hakomori, Chemistry and Physics of Lipids, Vol. 42, pp. 209-33). Among other things it was found that

- the carbohydrate structures are important for the stability, activity, localisation, immunogenicity and degradation of glycoproteins;
- carbohydrates are antigenic determinants (for example blood group antigens);
- carbohydrates function as receptors when bound to cell surfaces for pathogens, proteins, hormones, toxins and during cell-cell interactions;
- carbohydrates are important to oncogenesis, since specific oligosaccharides have been found to be cancer-associated antigenic determinants;
- frequently only a smaller sequence (di- or trisaccharide) of the carbohydrate part of the glycoconjugate is required for full biological activity (e.g. receptor activity).

Universities and industry are at present working intensely on developing the use of biologically active oligosaccharides within a number of different fields, such as

- novel diagnostics and blood typing reagents
- highly specific materials for affinity chromatography
- cell specific agglutination reagents
- targeting of drugs
- monoclonal antibodies, specific against e.g. cancer-associated structures
- therapy Besides the above-mentioned fields, a considerable future market is envisaged for fine chemicals based on biologically active carbohydrates.

The organic chemical techniques used today for synthesis of these carbohydrate structures require an extensive protective group chemistry with many steps of synthesis and expensive catalysts. Low total yields are obtained in those complicated reaction schemes and the technique is not favorable, especially for larger scale work.

Enzymes are nature's own catalysts with many attractive characteristics, such as high stereo-, regio- and substrate selectivity as well as high catalytic efficiency under mild conditions. Today, great hopes are therefore placed in being able to utilize enzymes for large-scale selective synthesis of oligosaccharides with fewer reaction steps and consequently higher total yields than by organic chemical methodology.

Both hydrolases (glycosidases. EC 3.2) and glycosyltransferases (EC 2.4) can be used for synthesis (glycosidases: see Nisizawa et al. in The Carbohydrates, Chemistry and Biochemistry, 2nd Ed., Vol. IIA, pp. 242-290, Academic Press, New York (1970)). With glycosidases reversed hydrolysis (equilibrium reaction) or transglycosylation (kinetic reaction) are often used to obtain synthesis (see e.g. K.G.I. Nilsson, Carbohydrate Res., Vol. 167, pp. 95-103 (1987)). With transferases a nucleotide sugar (UDP-Gal, CMP-Sia, UDP-GalNAc, GDP-Fuc, etc), which is relatively expensive, is used as donor. Both types of enzymes have advantages. Glycosidases are abundant and can often be used directly without purification, glycosyltransferases show high regio- and acceptor-selectivity. However, both types of enzymes have disadvantages when used for synthesis. Glycosidases have a low or often wrong regioselectivity which may result in complicated product mixtures and thus purification problems. As a result glycosidases are often not suitable for synthesis of higher oligosaccharides. Glycosyltransferases are often present in small amounts in living cells and are thus often of low availability. Furthermore, as mentioned above, the transferases are cofactor dependent.

One of the objects of the present invention is to use the properties of glycosidases and glycosyltransferases in a favorable way for efficient synthesis of oligosaccharides. This is achieved according to the invention by combining glycosidase-catalysed synthesis of an oligosaccharide compound with glycosyltransferase-catalysed synthesis of the final, higher oligosaccharide. An easily available glycosidase is thus used for synthesis of the shorter oligosaccharide compound and a regiospecific enzyme (i.e. glycosyltransferase) is used when a higher regioselectivity is required, i.e., for synthesis of the final oligosaccharide. This is illustrated in the following scheme (which is not intended to restrict the scope of the invention);

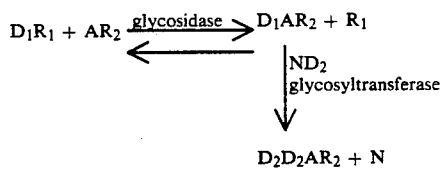

($D_1R_1$ symbolizes donor saccharide (oligosaccharide, glycoside) with $\alpha$- or $\beta$-bound aglycon ($R_1$), $D_1AR_2$ is an O—, C—, N—, S— or F-glycoside of a di- or higher oligosaccharide, $ND_2$ is a suitable sugar nucleotide (CMP-Neu5Ac, UDP-Gal, UDP-GalNAc, GDP-Fuc, etc) and $D_2D_1AR_2$ is the final oligosaccharide product. The glycosidase reaction can also be an equilibrium reaction. More than one glycosidase and/or transferase can be used for synthesis of higher oligosaccharides.

The substrates are selected with regard to the oligosaccharide which is to be synthesized, and are often commercially available or can be synthesized by organic or enzymatic synthesis and therefore do not restrict the use of the invention.

The enzymes are selected with regard to the final oligosaccharide which is to be synthesized. The enzyme can be used in situ (especially several glycosidases) or after partial or complete purification (especially glycosyltransferases) from their natural environment. The enzyme may be used in soluble form or immobilized to a solid phase by e.g. adsorption, encapsulation, chelation, precipitation or covalent binding. Simultaneous use of glycosidase and glycosyltransferase in soluble form or immobilized to a solid phase (eventually co-immobilized) may be advantageous according to the invention facilitating the conversion of the intermediate oligosaccharide product (e.g. $D_1AR_2$ in the scheme above) to the final product oligosaccharide (e.g. $D_2D_1AR_2$ in the scheme above). In this way the method according to the invention gives important advantages compared to previous methods: purification of intermediary product is not necessary, secondary hydrolysis is minimized (i.e. higher yield) and trisaccharides or higher oligosaccharides can be synthesized in a minimum of "pots" (in some cases one-pot reactions). This is facilitated by the high acceptor specificity of most glycosyltransferases: the transferase in the scheme above does not react with the wrong isomer of $D_1AR_2$ or with $D_1R_1$. Thus, for example, CMP-N-acetyl-neuraminate-$\beta$-D-galactoside ($\alpha$2-3)sialyltransferase (EC 2.4.99.4) prefers Gal$\beta$1-3GalNAcR over Gal$\beta$1-3GlcNAcR as acceptor and Gal$\beta$1-4GlcNacR and GalR are poor acceptors (Sadler et al., J. Biol. Chem., Vol. 254, pp. 4434-43). If glycosides ($AR_2$) are used as acceptors in the glycosidase-catalysed reaction, a product glycoside is obtained which is easy to purify since no anomerisation of the product glycoside occurs. Furthermore, the same glycosidase may be used for predominant synthesis of several isomers, since the regioselectivity may be changed by the use of different aglycons and by changing the configuration ($\alpha$- or $\beta$-) of the glycosidic linkage between for example A and $R_2$ in the scheme above (K.G.I. Nilsson, Carbohydrate Res., Vol. 167, pp. 95-103). The aglycon $R_2$ may be an organic compound of varying type (aliphatic, aromatic, heterocyclic, or variations thereof) which is O—, N—, C—, S-glycosidically bonded to A. $R_2$ may also be glycosidically bound F or an —OH group.

As examples of suitable organic aglycons mention may be made of $CH_3(CH_2)n$-groups (methyl, ethyl, etc.), 2-bromoethyl, allyl, trimethylsilylethyl, 2-(2-carbometoxiethylthio)ethyl, amino acids (seryl, threonyl, asparaginyl, etc) or derivatives thereof, peptides, phenyl, bensyl, nitroophenyl, lipids and analogs thereof.

Examples of $\alpha$- and $\beta$-glycosidases which may be used according to the invention are D-mannosidases, D-galactosidases, L-fucosidases, N-acetyl-D-galactosaminidases, hexosaminidases and other glycosidases in the EC group 3.2 (Enzyme Nomenclature, Academic Press, 1984).

Examples of sialyl-, galactosyl-, fucosyl-, N-acetyl-glucosaminly-, N-acetyl-galactosaminyl- and mannosyl-transferases which can be used according to the invention are found in the EC group 2.4 (Enzyme Nomenclature, Academic Press, 1984). Recombinant enzymes can be used according to the invention.

The synthesis method according to invention is generally applicable to the synthesis of oligosaccharide sequences included in glycoconjugates (see examples of structures given in references on page 1 one above). Of special interest are the minutest fragments of these structures, which are sufficient to transfer biological activity and the choice of Di and A in the scheme above is determined by this.

Examples of interesting structures are blood group determinants, cancer-associated oligosaccharide structures and structures with biological receptor activity (see references on p. 1).

Some examples of how the invention may be used in actual practice are described in the following Examples, which however are in no way intended to restrict the scope of the invention (abbreviations according to IUPAC-IUB's recommendations, J. Biol. Chem., Vol. 257, pp. 3347-3354 (1982)).

EXAMPLE 1

Synthesis of NeuSAc($\alpha$2-3)Gal($\beta$1-3)GalNAc($\beta$)-OEtBr. GalNAc($\beta$)-OEtBr was obtained by mixing GalNAc($\beta$)-OPhNO$_2$-p (1.2 g) in 100 ml sodium phosphate buffer (0.05 M, pH 5.2) with 2-bromoethanol (10 ml) and adding N-acetyl-$\beta$-D-glucosaminidase (EC 3.2.1.30; 70 U).

After 48 h at room temperature 500 mg of GalNAc($\beta$)-OEtBr was isolated by column chromatography (Kieselgel 60, Merck; methylene chloride-methanol-water). GalNAc($\beta$)-OEtBr (400 mg) and Gal($\beta$)-OPhNO$_2$-o (1 g) were suspended in 13 ml 0.03 M sodium phosphate buffer, pH 6.5, and dimethylformamide (4 ml) and 7.2 ml $\beta$-D-galactosidase from bovine testes (2 U; Sigma) were added. After 4 days at 37° C. the product was isolated by column chromatogrphy as above. The fractions containing product was acetylated and further purified by column chromatography. Deacetylation gave 40 mg pure Gal($\beta$1-3)GalNAc($\beta$)-OEtBr which was characterized with NMR ($^{13}$C, $^1$H).

CMP-Neu5Ac (4 mg, enzymatically prepared) and the above disaccharide (4 mg) were dissolved in 2 ml 0.1 M MES-HCl, pH6.7, CMP-N-acetylneuraminyl-$\beta$-D-galactoside ($\alpha$2-3)sialyltransferase (EC 2.4.99.4, porcine submaxillary gland, 20 mU. 0.17 ml, Genzyme) was added together with 10 $\mu$l Triton X-100 and 2 mg bovine serum albumin. More CMP-Neu5Ac (4 mg) was added after 20 h. After a total reaction time of 72 h at 37° C. 5 mg of Neu5Ac($\alpha$2-3)Gal($\beta$1-3)GalNAc($\beta$)-OEtBr was isolated by column chromatography (Kieselgel 60, acetonitrile-2-propanol-2.5 M NH$_4$OH and Sephadex G-15). This product was pure according to NMR ($^1$H, $^{13}$C) and the structure was confirmed by methylation analysis.

EXAMPLE 2

Synthesis of Neu5Ac($\alpha$2-3)Gal($\beta$1-3)GlcNAc($\beta$)-OMe.

This substance was prepared analogously. $\beta$-D-galactoside ($\alpha$2-3) sialyltransferase (0.34 ml, 40 mU) was added to 0.7 ml 0.1 M MES-CHl, pH 6.7, which contained 30 mg Gal($\beta$1-3)GlcNAc($\beta$)-OMe (synthesized as described above for Gal($\beta$1-3)GalNAc($\beta$)-OEtBr but with GlcNAc($\beta$)-OMe as acceptor), 10 mg CMP-Neu5Ac, 5 $\mu$l Triton X-100 and 1 mg albumin. More CMP-Neu5Ac (10 mg) was added after 30 h. After five days at 37° C. column chromatography as described above gave 10 mg Neu5Ac($\alpha$2-3)Gal($\beta$1-3)GlcNAc($\beta$)-OMe which was pure according to NMR. The structure was confirmed with NMR and methylation analysis.

The acceptor selectivitity of the glycosyltransferases in several of the examples is such that co-immobilized glycosidase and glycosyltransferase can be used and in some cases one-pot reactions are possible (enzymes, glycosidase substrate and nucleotide sugar which are used are mixed directly or nucleotide sugar and glycosyltransferase are added after the glycosidase). In some cases the glycosidase product is only partially purified (i.e. Sephadex G10 column) before further reaction with the glycosyltransferase.

EXAMPLE 3

Synthesis of NeuSAcα2-3Galβ1-4GlcNAcβ-OMe

β-D-Galactosidase from bovine testes was used as in Example 2 for synthesis of Galβ1-4GlcNAc-OMe (the enzyme gives this isomer in addition to the β1-3 isomer; β-galactosidas from another source (lactobacillus or sporobolomyces) is used for more specific synthesis of Galβ1-4GlcNAc-OMe).

α2-3Sialyltransferase (EC 2.4.99.5) is used for the sialylation.

EXAMPLE 4

Synthesis of NeuSAcα2-6Galβ1-4GlcNAcβ-OMe

Synthesis as in example 3 but with α2-6sialyltransferase (EC 2.4.99.1).

EXAMPLE 5

Synthesis of NeuSAcα2-3Galβ1-3(NeuSAcα2-6)GalNAcα-OEtBr

Synthesis as in example 1 using GalNAcα-OEtBr as acceptor and in addition α2-6sialyltransferase (EC 2.4.99.7) as catalyst.

EXAMPLE 6

Synthesis of Fucα1-2Galβ1-3GlcNAcβ-OMe

Synthesis as in example 2 but with α1-2fucosyltransferase (EC 2.4.1.69) and GDP-Fuc as donor instead of α2-3sialyltransferase and CMP-Neu5Ac, respectively.

EXAMPLE 7

Synthesis of Fucα1-2Galβ1-4GlcNAcβ-OMe

Synthesis as in example 6 but with β1-4 isomer as acceptor.

EXAMPLE 8

Synthesis of Galβ1-4(Fucα1-3)GlcNacβ-OMe

Synthesis as in example 7 but with α2-3fucosyltransferase (EC 2.4.1.152 or EC 2.4.1.65 with which also Galβ1-3(Fucα1-4)GlcNAc can be synthesized as in example 6) as catalyst.

EXAMPLE 9

Synthesis of Galα1-3Galβ1-4GlcNAcβ-OMe

Synthesis as in example 3 but instead of EC 2.4.99.6 and CMP-Neu5Ac, α1-3galactosyltransferase (EC 2.4.1.151) and UDP-Gal are used.

EXAMPLE 10 and 11

GalNAcα1-3Galβ1-3GlcNAcβ-OMe (10) and GalNAcα1-3Galβ1-4GlcNAcβ-OMe (11)
2 2
Fucα1 Fucα1

Synthesis as in example 6 (substance 10; blood group A, type 1) and as in example 7 (substance 11; blood group A, type 2), respectively, and in addition to EC 2.4.1.69, α1-3N-acetylgalactosaminyltransferase (EC 2.4.1.40, from e.g. human milk) and UDP-GalNAc are used.

EXAMPLE 12 and 13

Galα1-3Galβ1-3GlcNAcβ-OMe (12) och Galα1-3Galβ1-4GlcNAcβ-OMe (13).
2 2
Fucα1 Fucα1

Substance 12 and 13 (blood group B, type 1 and 2, respectively) are synthesized as 10 and 11, respectively, but with EC 2.4.1.37 and UDP-Gal instead of EC 2.4.4.1.40 and UDP-GalNac.

In the above examples various methyl and bromoethyl glycosides were prepared. The expert can easily synthesize other interesting glycosides exemplified in the description and choose optimal conditions for the reactions. The sugar nucleotides are obtained with e.g. enzymatic synthesis (nucleotidyltransferase+nucleotide +monosaccharid (or monosaccharide-1-phosphate) for example CTP+Neu5Ac+CMP-Neu5Ac-syntas (EC 2.7.7.43).

I claim:

1. A method of synthesizing an oligosacchride compound product which either consists of or is a fragment or analog of the carbohydrate part in a glycoconjugate, said method consisting essentially of
   reacting
   (a) at least one donor substance comprising a oligosaccharide or monosaccharide or glycoside,
   (b) at least one acceptor substance comprising a monosaccharide, oligosaccharide, glycoside, or saccharide analog,
   (c) at least one nucleotide sugar which is a donor substance, and
   (d) at least one E.C. group 3.2 glycosidase and at least one E.C. group 2.4 glycosyltransferase, to synthesize said oligosaccharide compound product, whereby said glycosidase enters into a transglycosylation or reversed hydrolysis reaction to thereby synthesize said oligosaccharide compound product.

2. The method as claimed in claim 1, wherein the carbohydrate portion of said donor substance in (a) or (c) and said acceptor substance in (b) is at least one member selected form the group consisting of D-galactose, D-mannose, N-acetylneuraminic acid, N-acetyl-D-galactosamine, N -acetyl-D-glucosamine, L-fucose, and analogs thereof.

3. The method as claimed in claim 1, wherein said acceptor substance is a glycoside in which the aglycon is glycosidically bound fluorine or an O—, N—, C— or S— glycosidically bound aliphatic or aromatic compound.

4. The method as claimed in claim 3, wherein said aliphatic or aromatic compound is selected from the group consisting of allyl-, methyl-, ethyl-, bromoethyl-, epoxi-, trimethylsilylethyl-, phenyl-, benzyl-, and a nitrophenyl group.

5. The method as claimed in claim 1, wherein said nucleotide sugar is at least one member selected from the group consisting of CMP-Neu5Ac, GDP-Fuc, UDP-Gal, UDP-GlcNAc, and UDP-GalNAc.

6. The method as claimed in claim 1, wherein at least one of said glycosidase and at least one of said glycosyltranferase are in soluble or immobilized form and are used simultaneously for the synthesis of said oligosaccharide compound.

7. The method as claimed in claim 1, wherein Neu5Acα2-3Galβ1-3GalNAc-R and Neu5Acα2-3Galβ1-3GlcNAc-R are synthesized employing β-D-galactosidase and β-D-galactoside (α2-3)sialyl-transferase, wherein R is a glycosidically bound aglycon.

8. The method as claimed in claim 1, wherein one of Galβ1-3(Fucα1-4)GlcNAc-R, Neu5Acα2-6Galβ1-4GlcNAc-R, Neu5Acα2-3Galβ1-3(Neu5Acα2-6)GalNAc-R, Fucα1-2Galβ1-3GlcNAc-R, Fucα1-2Galβ1-4GlcNAc-R, Galβ1-4(Fucα1-3)GlcNac-R, Galα1-3Galβ1-4GlcNAc-R, GalNAcα1-3Galβ1-3GlcNAc-R, GalNAcα1-3Galβ1-4GlcNAc-R,

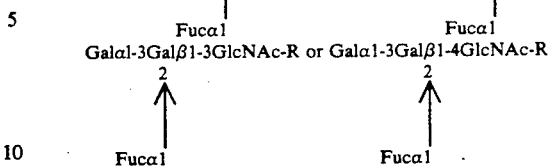

is synthesized, wherein R is a glycosidically bound aglycon.

9. The method as claimed in claim 1, wherein said oligosaccharide compound having bio-specific affinity to another substance is synthesized and isolated.

10. A method for enzymatic synthesis of an oligosaccharide compound consisting essentially of reacting a donor substance, wherein said donor substance is an oligosaccharide or monosaccharide or glycoside and an acceptor substance with α- or β-bound aglycon, with an E.C. group 3.2 glycosidase to form an oligosaccharide compound which is an O—, C—, N—, S— or F-glycoside of a di- or higher oligosaccharide which is reacted with a sugar nucleotide and at least one E.C. group 2.4 glycosyltransferase to form the final, higher oligosaccharide product.

11. The method according to claim 10, which further comprises separating said product from the reaction mixture.

* * * * *